(12) United States Patent
Rice et al.

(10) Patent No.: US 10,143,488 B2
(45) Date of Patent: Dec. 4, 2018

(54) ECCENTRIC PASS-THRU CUTTER

(71) Applicant: Covidien LP, Mansfield, MA (US)

(72) Inventors: Alexander Rice, Hutchinson, MN (US); Victoria Schuman, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 453 days.

(21) Appl. No.: 14/102,101

(22) Filed: Dec. 10, 2013

(65) Prior Publication Data
US 2014/0194912 A1   Jul. 10, 2014

Related U.S. Application Data

(60) Provisional application No. 61/736,192, filed on Dec. 12, 2012.

(51) Int. Cl.
*A61B 17/3207* (2006.01)

(52) U.S. Cl.
CPC .. *A61B 17/320758* (2013.01); *A61B 17/3207* (2013.01); *A61B 17/320783* (2013.01); (Continued)

(58) Field of Classification Search
CPC .......... A61B 17/3205; A61B 17/32056; A61B 17/3207; A61B 17/320708; A61B 17/320725; A61B 17/32075; A61B 17/320758; A61B 17/320783; A61B 17/320016; A61B 17/32002; A61B 2017/320716; A61B 2017/320733; A61B 2017/320741; A61B 2017/320766; A61B 2107/320775; A61B 2017/320791; A61B 2017/320004; A61B 2017/320008; A61B 2017/320024; A61B 2017/320028; (Continued)

(56) References Cited

U.S. PATENT DOCUMENTS 4,942,788 A   7/1990 Farr et al.
5,632,755 A   5/1997 Nordgren et al.
(Continued)

FOREIGN PATENT DOCUMENTS

DE   91110122 U1   11/1991

OTHER PUBLICATIONS

English Translation of DE 9111012.*
(Continued)

*Primary Examiner* — Darwin Erezo
*Assistant Examiner* — Katherine Schwiker
(74) *Attorney, Agent, or Firm* — Stinson Leonard Street LLP

(57) ABSTRACT

A catheter includes an elongate catheter body configured for insertion into a body lumen of a subject. A cutter is located generally at a distal end of the catheter body for rotation generally about a longitudinal axis of the cutter. An eccentric opening in a distal end portion of the cutter defines an angled cutting edge for cutting material from a wall of the body lumen. A center of the opening is offset from the longitudinal axis of the cutter. A cavity extends from the opening through the cutter from the distal end portion to a proximal end portion to allow material cut by the cutter to pass through the cutter into an interior passage of the catheter body for removal from the body lumen.

12 Claims, 13 Drawing Sheets

(52) U.S. Cl.
CPC ............. *A61B 2017/320766* (2013.01); *A61B 2017/320775* (2013.01); *A61B 2017/320791* (2013.01)

(58) Field of Classification Search
CPC .. A61B 2017/32004; A61B 17/320026; A61B 2017/320032; A61B 2017/00685; A61B 2017/2927; A61B 2017/2929
USPC .................................................. 606/167–171
See application file for complete search history.

(56) References Cited

U.S. PATENT DOCUMENTS

| | | | |
|---|---|---|---|
| 7,981,128 B2* | 7/2011 | To ..................... | A61B 17/32075 606/159 |
| 2007/0276419 A1* | 11/2007 | Rosenthal ........ | A61B 17/32002 606/159 |
| 2008/0065124 A1 | 3/2008 | Olson | |
| 2010/0030216 A1 | 2/2010 | Arcenio | |
| 2010/0191266 A1 | 7/2010 | Oliver et al. | |
| 2010/0280407 A1* | 11/2010 | Polster ............... | A61B 10/0266 600/566 |
| 2011/0144673 A1 | 6/2011 | Zhang et al. | |
| 2011/0306995 A1* | 12/2011 | Moberg ........... | A61B 17/32078 606/159 |

OTHER PUBLICATIONS

International Search Report and Written Opinion dated Mar. 7, 2014 for Application No. PCT/US2013/073546, 11 pages, European Patent Office, Rijswijk, Netherlands.

* cited by examiner

ECCENTRIC PASS-THRU CUTTER

CROSS-REFERENCE TO RELATED APPLICATION

This application claims the benefit of priority under 35 U.S.C. § 119 to U.S. patent application No. 61/736,192, titled ECCENTRIC PASS-THRU CUTTER, which was filed on Dec. 12, 2012, and which is incorporated herein by reference in its entirety for all purposes.

BACKGROUND

The present invention generally relates to a debulking catheter for removing material from a body lumen.

Vascular disease frequently arises from the accumulation of atheromatous material on the inner walls of vascular lumens, particularly arterial lumens of the peripheral and other vasculature, especially peripheral arteries, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease can be treated in a variety of ways, including drugs, bypass surgery, and a variety of catheter-based approaches, including those which rely on intravascular debulking or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

It is desirous to provide catheters which can access small, tortuous regions of body lumens and which can remove tissue and/or other occluding materials from within body lumens in a controlled fashion. In one instance, it may be desired to provide atherectomy catheters which can facilitate capturing atheromatous materials. The catheters and methods are for use in a variety of body lumens, including but not limited to coronary, peripheral, and other arteries, and other body lumens.

SUMMARY

In one aspect, a catheter generally comprises an elongate catheter body configured for insertion into a body lumen of a subject. The catheter body has opposite distal and proximal ends, a longitudinal axis extending between the distal and proximal ends, and an interior passage extending along the longitudinal axis. A cutter has a proximal end portion, a distal end portion, and a longitudinal axis extending between the proximal and distal end portions. The cutter is located generally at the distal end of the catheter body for rotation generally about the longitudinal axis of the cutter. An eccentric opening in the distal end portion of the cutter defines an angled cutting edge for cutting material from a wall of the body lumen. A center of the opening is offset from the longitudinal axis of the cutter. A cavity extends from the opening through the cutter from the distal end portion to the proximal end portion to allow material cut by the cutter to pass through the cutter into the interior passage of the catheter body for removal from the body lumen.

In another aspect, a catheter generally comprises an elongate catheter body configured for insertion into a body lumen of a subject. The catheter body has opposite distal and proximal ends, a longitudinal axis extending between the distal and proximal ends, and an interior passage extending along the longitudinal axis. A cutter has a proximal end portion, a distal end portion, and a longitudinal axis extending between the proximal and distal end portions. The cutter is located generally at the distal end of the catheter body for rotation generally about the longitudinal axis of the cutter. The distal end portion has an angled cutting edge for cutting tissue from a wall of the body lumen. The angled cutting edge is angularly offset from the longitudinal axis of the cutter and extends at a non-orthogonal angle with respect to the longitudinal axis of the cutter.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
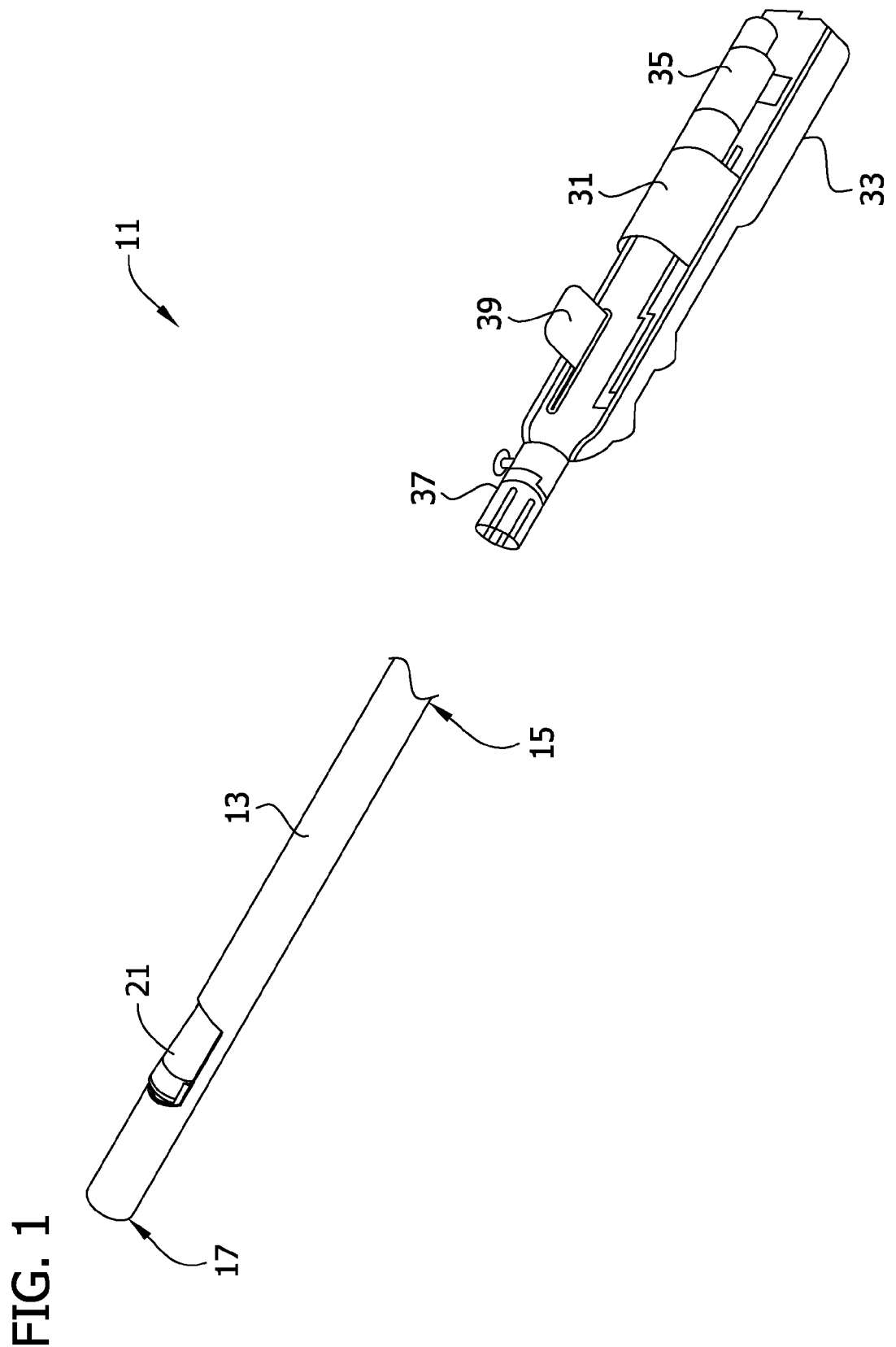
FIG. 1 is a fragmentary perspective of a debulking catheter with parts of a handle removed to show internal construction.

Referring now to the drawings, a debulking catheter that removes tissue from a body lumen wall is disclosed. The catheter is suitable for use with atherectomy catheters for removing (i.e., excising) an atheroma (i.e., plaque) from an arterial wall. The catheter may also be suitable for treating stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Debulking of such material can thus be beneficial to maintain patency of the body lumen. While the remaining discussion is directed toward components of atherectomy catheters for debulking and passing through atheromatous or thrombotic occlusive material in an artery, it will be appreciated that the components may be employed with other types of debulking catheters for removing and/or passing through a variety of occlusive, stenotic, or hyperplastic material in a variety of body lumens.

Figure 2:
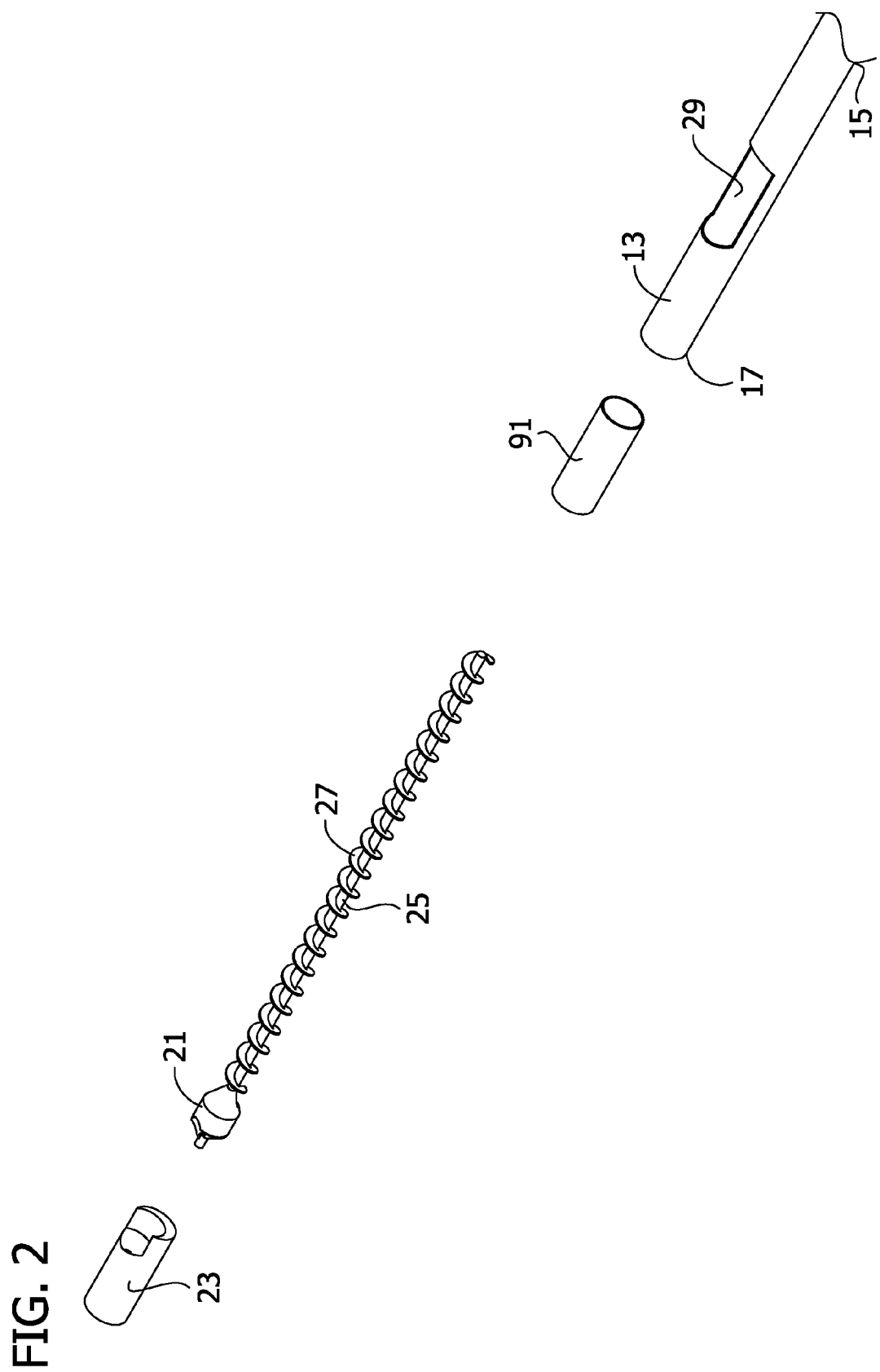
FIG. 2 is a fragmentary exploded view of a distal end portion of the catheter.
Figure 3:
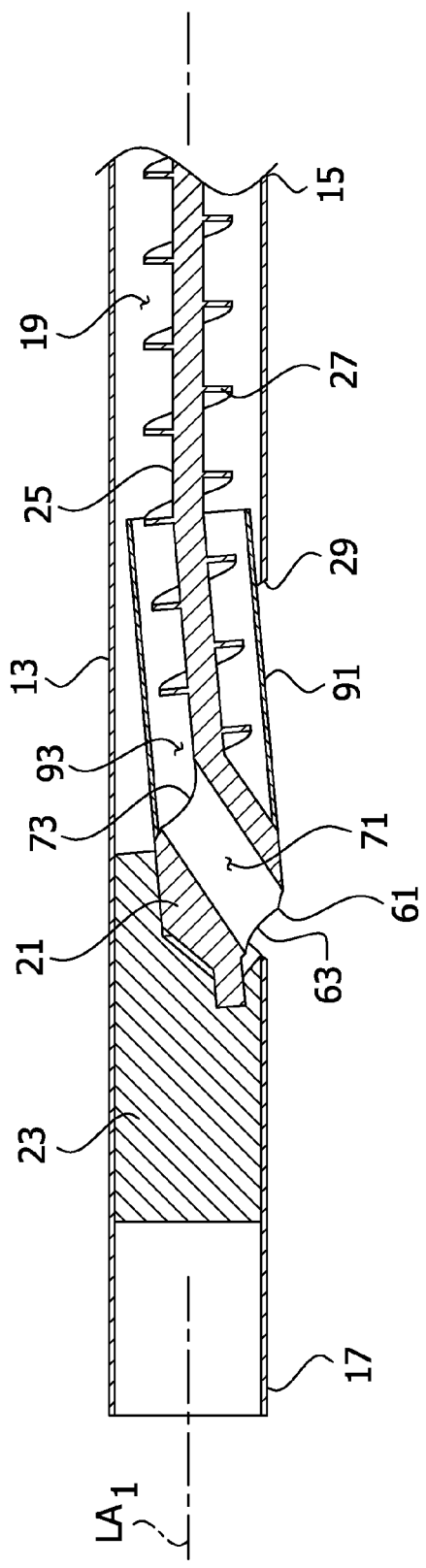
FIG. 3 is a fragmentary section of a distal end portion of the catheter.

Referring now to FIGS. 1-3, an atherectomy catheter is generally indicated at 11. The catheter comprises an elongate tubular catheter body or tube 13 having a longitudinal axis $LA_1$, a proximal end portion 15 and a distal end portion 17. The majority of the catheter tube 13, including the proximal end portion 15, may be generally flexible to permit the catheter tube 13 to bend and flex facilitating insertion and movement of the catheter 11 in a body lumen B of a patient. A lumen 19 extends axially through the catheter tube 13.

Figure 4:
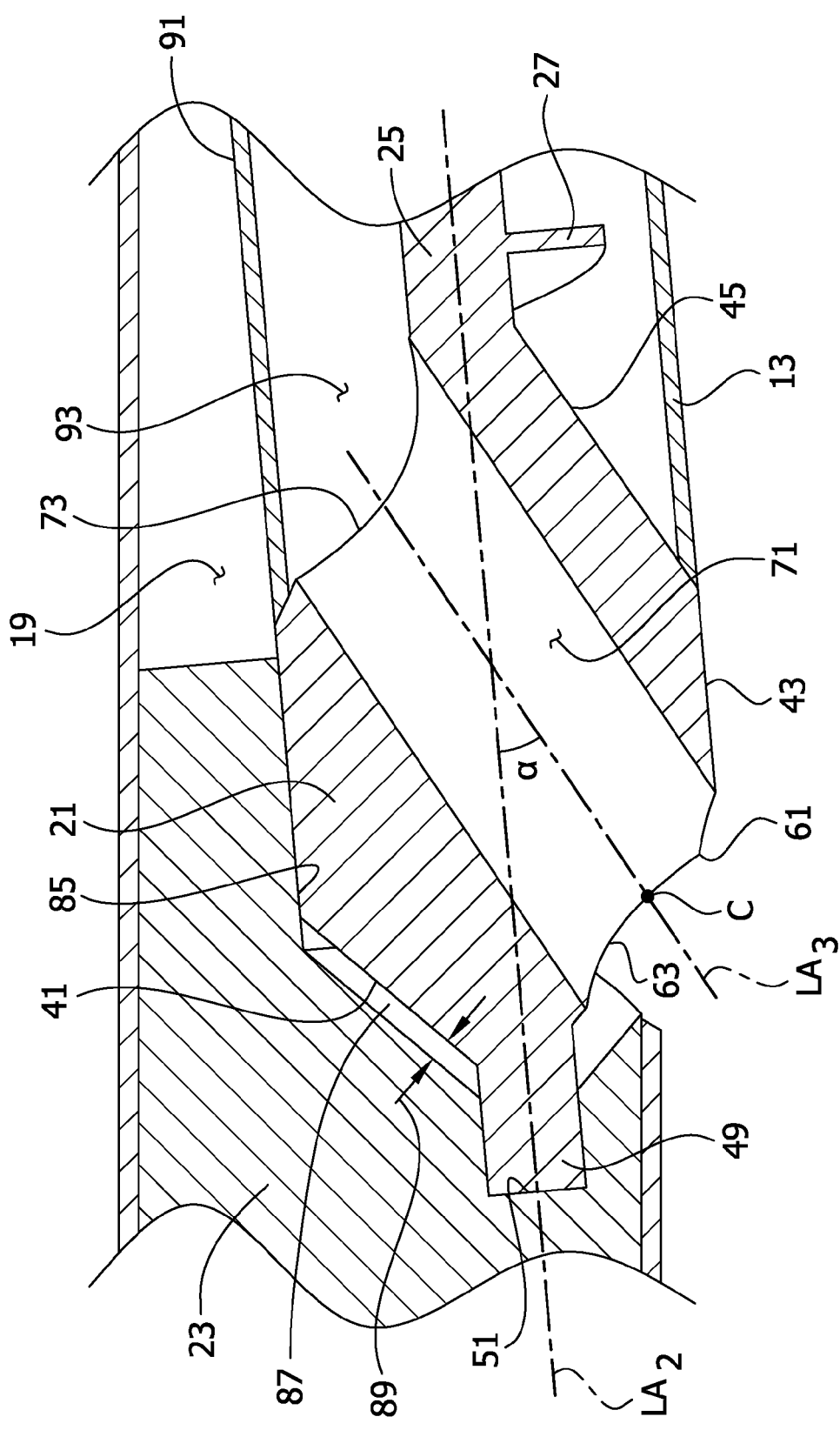
FIG. 4 is an enlarged detail of the section of FIG. 3.

A rotatable cutter, generally indicated at 21, is at least partially received in the lumen 19 and is operatively connected to the distal end portion 17 of the catheter tube 13 for removing tissue from an arterial wall. A portion of the cutter 21 extends out of an opening 29 in the catheter tube 13 (FIGS. 2 and 3). As shown in the illustrated embodiment, a distal end portion of the cutter 21 is operatively connected to a cutter adaptor or bearing, generally indicated at 23. A distal end of a driveshaft 25 is operatively connected to a proximal end portion of the cutter 21 for selectively driving rotation of the cutter generally about a longitudinal axis $LA_2$ of the cutter (FIG. 4). The driveshaft 25 extends through the lumen 19 of the catheter tube 13 and includes an external helical thread 27 for transporting or moving removed tissue proximally within the lumen 19.

The shank of the driveshaft 25 (i.e., the part of the driveshaft not including the thread 27) is generally flexible and may be formed from one or more coils (e.g., stainless steel coil(s)), or a torque tube (e.g., a polyimide tube with a layer of braided stainless steel wire embedded therein). The body of the driveshaft 25 may have a very high torsional stiffness and sufficient tensile strength, but which is generally laterally flexible. Depending upon the desired torque transmission, diameter and flexibility, any of a variety of other materials and constructions may also be used.

In the illustrated embodiment, the helical thread 27 on the exterior of the driveshaft 25 extends along the length of the driveshaft and functions as a transport mechanism for transporting removed tissue proximally within the lumen 19 of the catheter tube 13. Accordingly, the threaded driveshaft 25 functions as an auger or a screw conveyer, whereby rotation of the driveshaft imparts rotation of the helical thread 27, which moves removed tissue proximally within the catheter tube 13. In the illustrated embodiment, the thread 27 is a right-handed thread (as viewed from the proximal end of the driveshaft 25), such that rotation of the driveshaft clockwise (as viewed from the proximal end of the driveshaft) transports the tissue proximally. The driveshaft thread 27 may extend back to the proximal end portion 15 of the catheter tube 13 and may empty into a tissue receptacle (not shown). The driveshaft thread 27 may also stop short of the proximal end portion 15 of the catheter tube 13. The thread 27 may be formed on the driveshaft 25 in any suitable manner. It is to be understood that cut tissue conveying systems other than the threads 27 may be used. Moreover, the conveying system could be entirely omitted.

In the illustrated embodiment, the cutter 21 and driveshaft 25 are formed as a single, one-piece construction. However, the cutter 21 can be formed as a separate piece from the driveshaft 25 and attached to the driveshaft such as by a threaded connection (not shown). The cutter 21 can also be connected to the driveshaft 25 in any other suitable manner. In the illustrated embodiment, and in particular FIG. 1, the cutter 21 is in a permanently deployed position. However, the cutter 21 can be operatively connected to a deployment mechanism (not shown) to move the cutter between a deployed or exposed position as shown in the figures, and a retracted position where the cutter is fully received in the lumen 19 of the catheter tube 13 so the catheter 11 can safely traverse a subject's vasculature when the cutter 21 is not in use.

Referring to FIG. 1, the proximal end portion of catheter 11, and in particular, the proximal end of the driveshaft 25 is operably connected to a cutter motor 31 (broadly, a cutter driver) to impart rotation of the driveshaft relative to the catheter tube 13. In one example, the cutter motor 31 is disposed within a handle 33 (shown with a cover removed in FIG. 1) that is releasably connectable to the proximal end of the catheter 11. For example, in addition to the cutter motor 31, the handle 33 may house a power source 35 (e.g., batteries) for the cutter motor 31, a microswitch (not shown) for activating the cutter motor, and a catheter connector 37 for use in connecting the motor to the proximal end of the driveshaft 25. In some embodiments, the cutter motor 31 can rotate the driveshaft 25 between 1,000 rpm and 10,000 rpm or more, if desired. The handle 33 may include one or more input devices, such as lever 39, which controls the major operations of the catheter 11, such as rotation of the driveshaft 25 and the cutter 21 via the cutter driver 31. It is understood that the driveshaft 25 may be driven in other ways.

As seen best in FIGS. 4-7, the rotatable cutter 21 has opposite proximal and distal end portions and a longitudinal axis $LA_2$ extending therebetween. The distal end portion of the cutter 21 has an angled surface 41 extending around the distal end of the cutter. More specifically, the surface 41 is in the shape of a helical cone. A cylindrical portion 43 extends proximally from the angled surface 41, and a tapering portion 45 extends proximally from the cylindrical portion 43. The tapering portion 45 connects the cutter 21 to the driveshaft 25. A post 49 at the distal end portion of the cutter 21 extends distally from the beveled surface 41 and is received in a recess 51 in the bearing 23. The bearing 23 is fixed to an inner wall of the catheter tube 13 and supports the distal end portion of the cutter. The post 49 is allowed to rotate in the recess 51 to permit the cutter 21 to rotate relative to the bearing 23.

Figure 5:
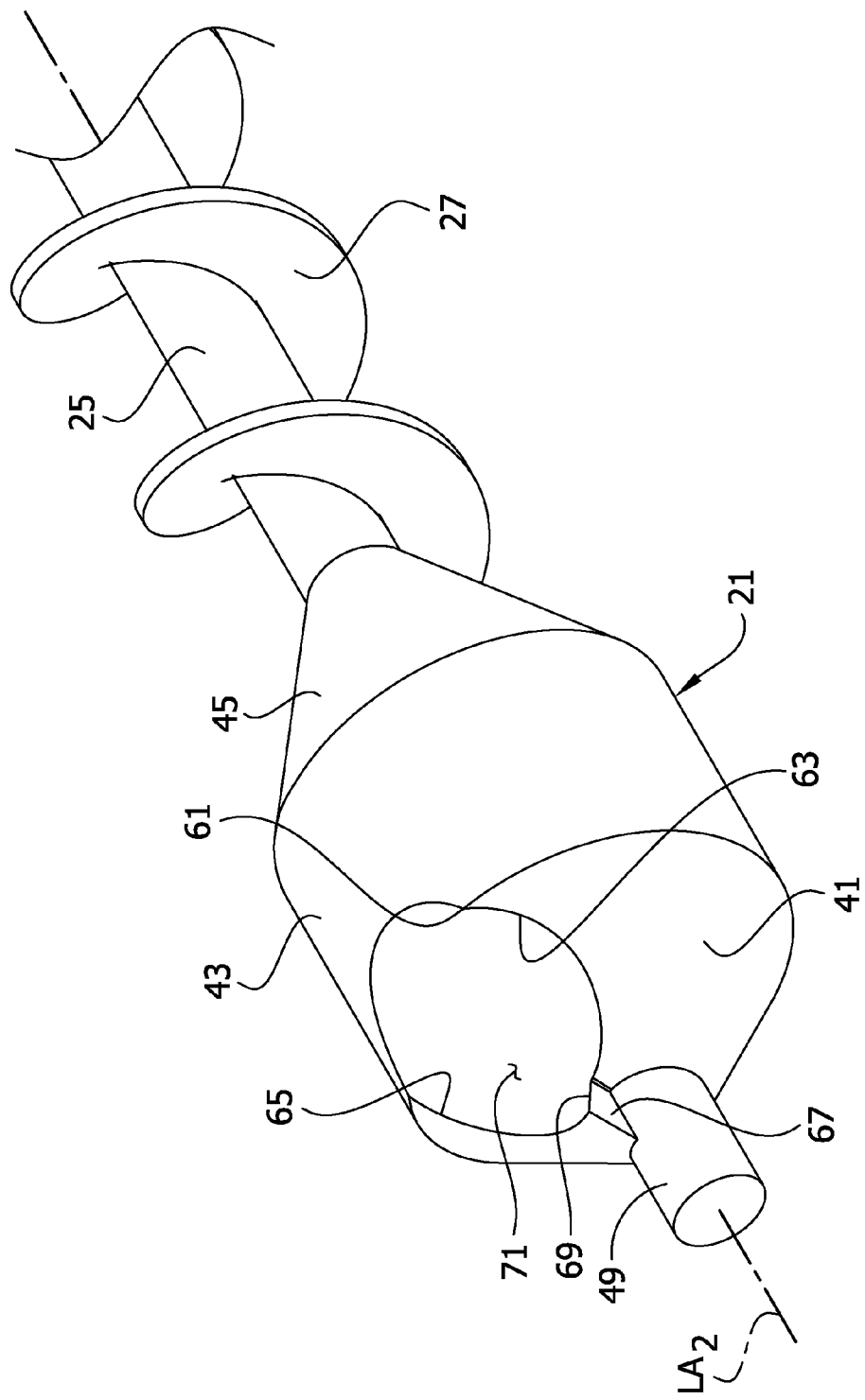
FIG. 5 is a fragmentary perspective of a cutter and driveshaft of the debulking catheter.
Figure 6:
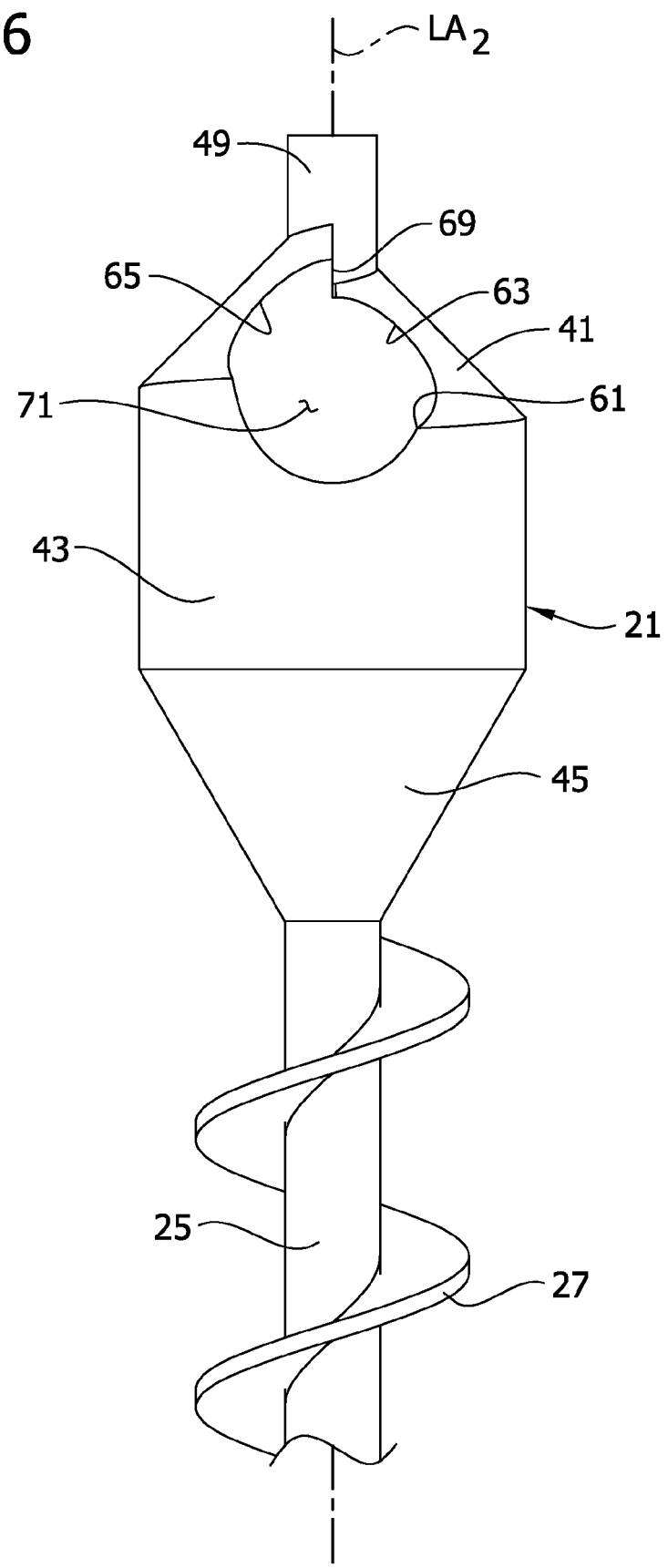
FIG. 6 is side elevation of the cutter and driveshaft in FIG. 5.
Figure 7:
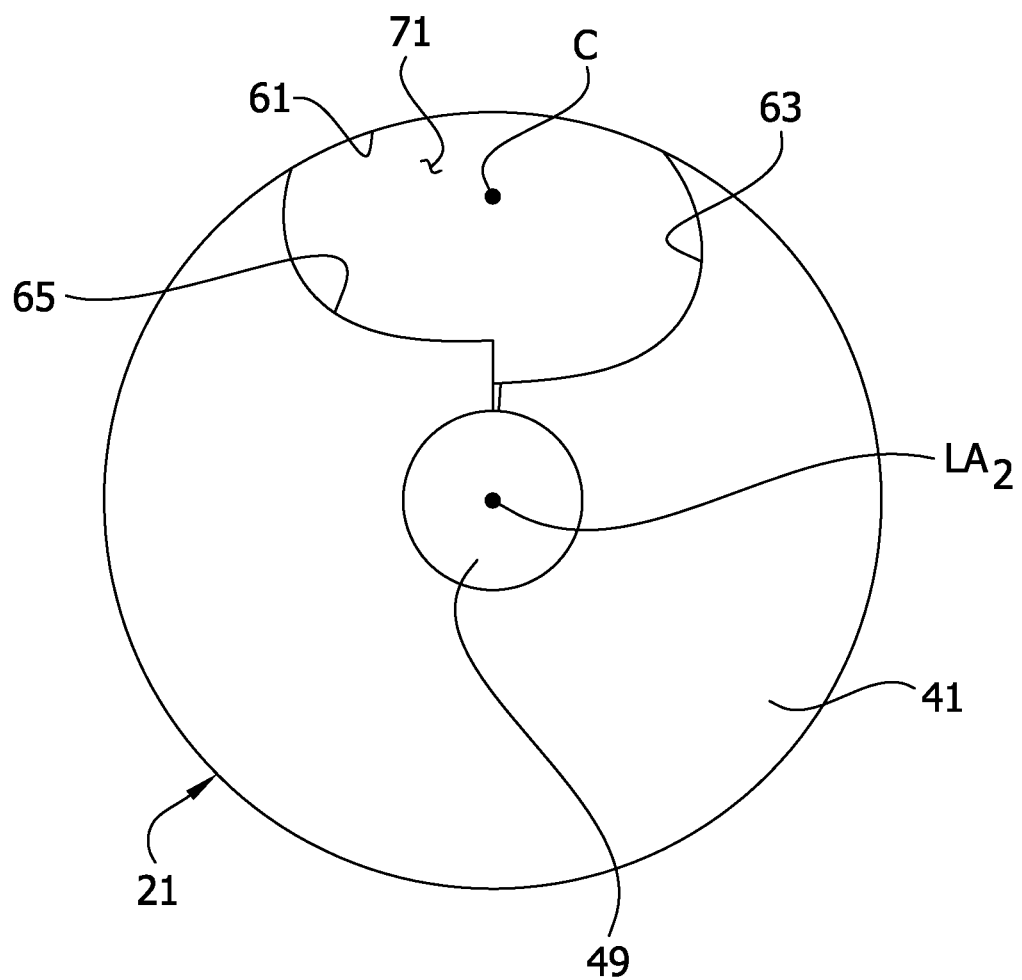
FIG. 7 is a front elevation of the cutter.

An eccentric opening 61 is formed in the angled surface 41 of the cutter 21. A center C of the opening 61 is offset from the longitudinal axis $LA_2$ of the cutter 21 so that the opening is not centered about the cutter's longitudinal axis (FIG. 4). The opening 61 forms an annular edge in the distal end portion of the cutter 21. The annular edge is generally separated into a leading edge portion 63 and a cutting edge portion 65. The leading edge portion 63 defines the portion of the annular edge which passes the atheroma in the body lumen B first when the cutter 21 is rotated. The cutting edge portion 65 passes the tissue second and is configured to grab and cut into the tissue as will be explained in greater detail below. The angled surface 41 has a helical contour forming a step down surface 67 (FIG. 5). A longitudinal edge 69 of the step down surface 67 connects the cutting edge portion 65 to the leading edge portion 63. As a result, the cutting edge portion 65 protrudes significantly further in a radial direction than the leading edge portion 63 so that the cutting edge portion can easily engage tissue in the body lumen B. Also, because the eccentric opening 61 is formed in the angled surface 41 of the cutter 21, the cutting edge portion 65 is disposed at a non-orthogonal angle with respect to the longitudinal axis $LA_2$ of the cutter.

A cavity 71 extends from the eccentric opening 61 through the cutter 21 from the distal end portion to the proximal end portion forming an outlet 73 in the proximal end portion. A longitudinal axis $LA_3$ of the cavity 71 extends through the center C of the opening 61 so that the cavity extends transversely through the cutter 21. In a preferred embodiment, the longitudinal axis $LA_3$ of the cavity 71 is skewed with respect to the longitudinal axis $LA_2$ of the cutter 21. In one embodiment, the longitudinal axis LA₃ of the cavity 71 extends generally at about a 45 degree angle α with respect to the longitudinal axis LA₂ of the cutter 21 (FIG. 4).

The cutter 21 may be formed as a single, one-piece construction, or may be formed from separate components secured to one another in a suitable manner, such as welding, soldering, adhesives, mechanical interference fit, threaded engagement and the like. As a non-limiting example, the cutter 21 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Figure 8:
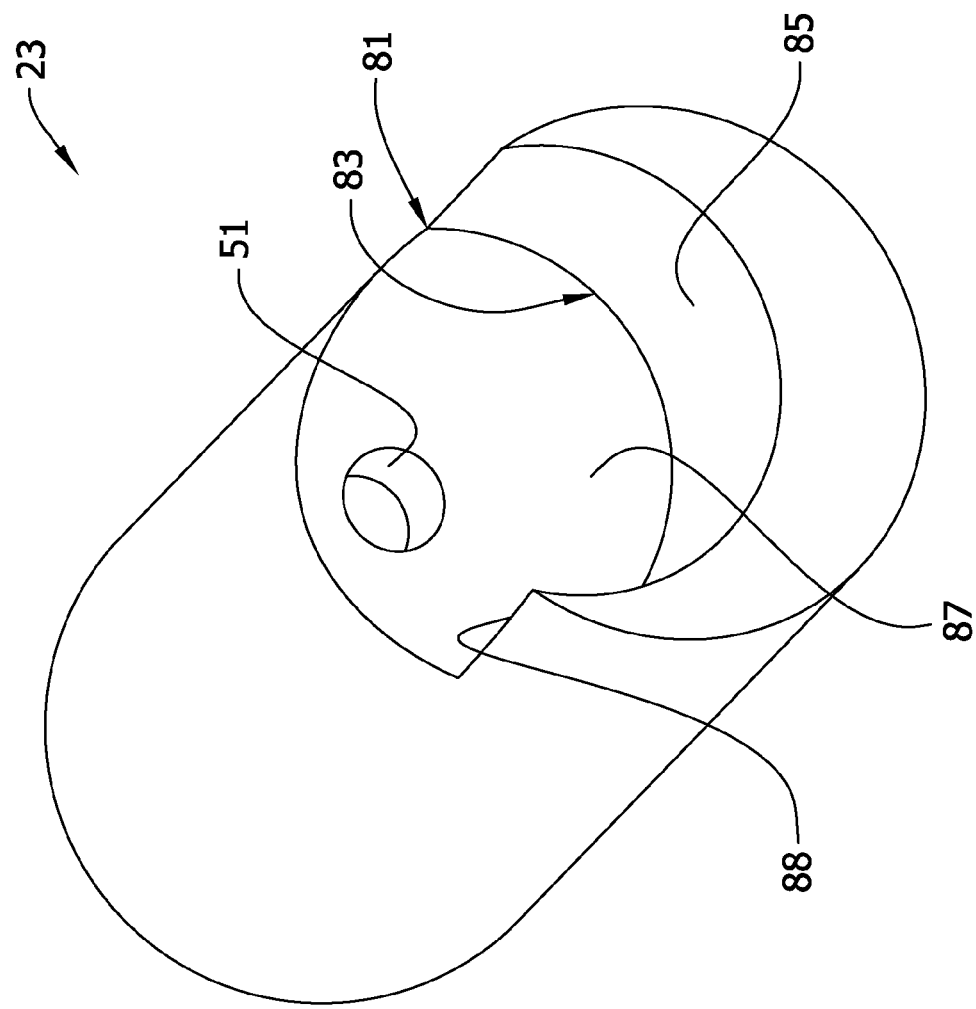
FIG. 8 is a perspective of a bearing of the catheter.
Figure 9:
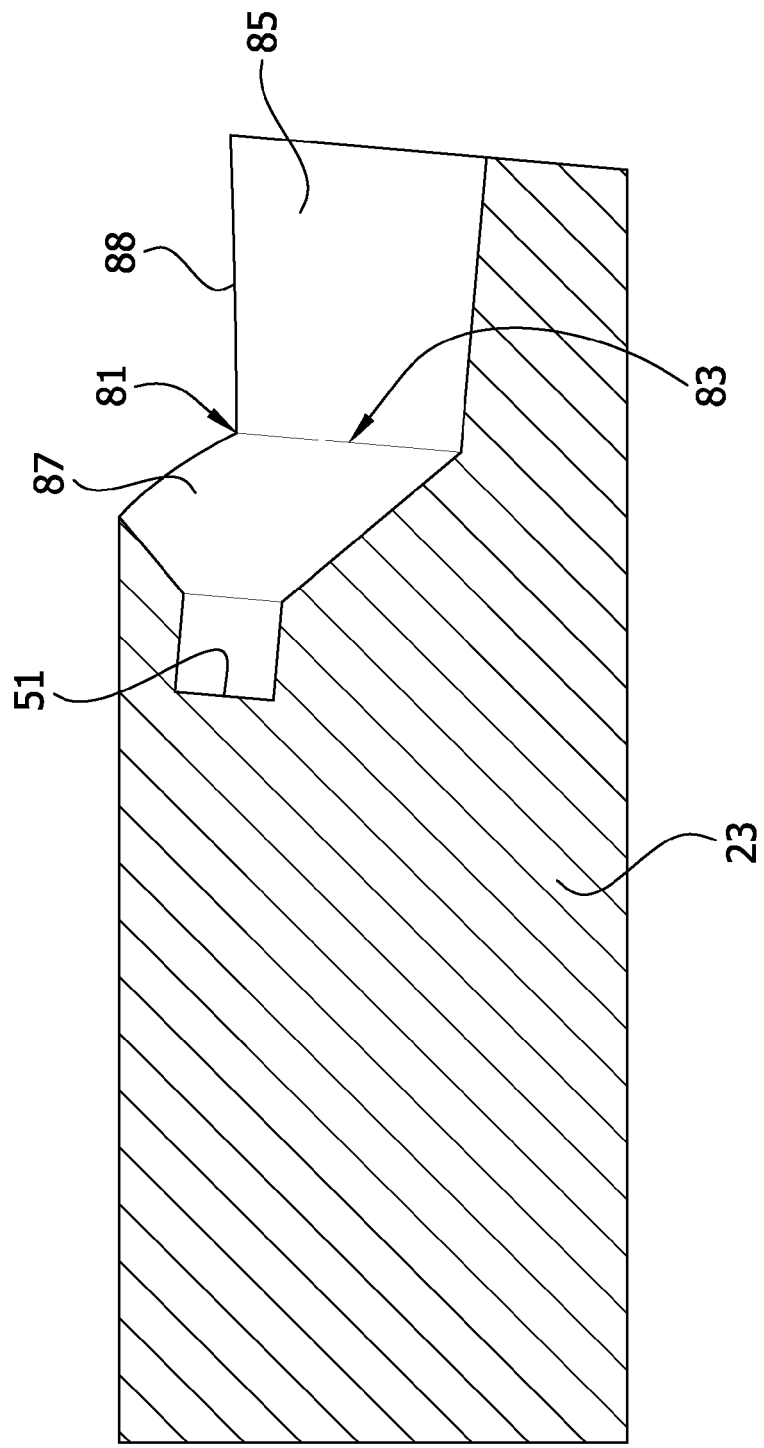
FIG. 9 is a section of the bearing.

Referring to FIGS. 8 and 9, the bearing 23 comprises a cylindrical member having a cutout 81 in an outer surface of the bearing. The cutout 81 fotnis a contoured inner surface 83 that generally opposes the cutter 21. The inner surface 83 comprises a support portion 85 generally opposing a portion of the cylindrical portion 43 of the cutter 21, and a shearing portion 87 generally opposing the angled surface 41 of the cutter (FIG. 4). A shearing edge 88 extends along one side of the cutout 81. The support portion 85 is disposed in close, sliding relation with the cylindrical portion 43 of the cutter 21 to guide rotation of the cutter. A clearance 89 is disposed between the shearing portion 87 of the bearing 23 and the beveled surface 41 of the cutter 21 when the cutter is in the rotational position shown in FIG. 4. As will be explained in greater detail below, the clearance 89 reduces to substantially zero when the cutting edge portion 65 of the cutter 21 is rotated into opposition with the shearing edge 88 of the bearing 23 allowing the shearing edge to cooperate with the cutting edge portion as the cutter rotates relative to the bearing to shear off pieces of tissue in the body lumen B.

Referring to FIGS. 2-4, a second bearing 91 is at least partially received in the lumen 19 of the catheter tube 13 and is attached to the proximal end portion of the cutter 21 at the junction between the cylindrical portion 43 and tapering portion 45. The second bearing 91 is a hollow cylindrical member having an interior space 93 that receives a portion of the cutter 21 and driveshaft 25. The interior space 93 of the second bearing 91 places the cutter outlet 73 and the lumen 19 of the catheter tube 13 in communication with each other. Therefore, as will be explained in greater detail below, when the cutter 21 cuts tissue in the body lumen B, the cut tissue can pass through the cutter into the interior space 93 of the second bearing 91 for transport to the proximal end 15 of the catheter tube 13 by the auger 27. The second bearing 91 can also have other configurations.

Figure 10A:
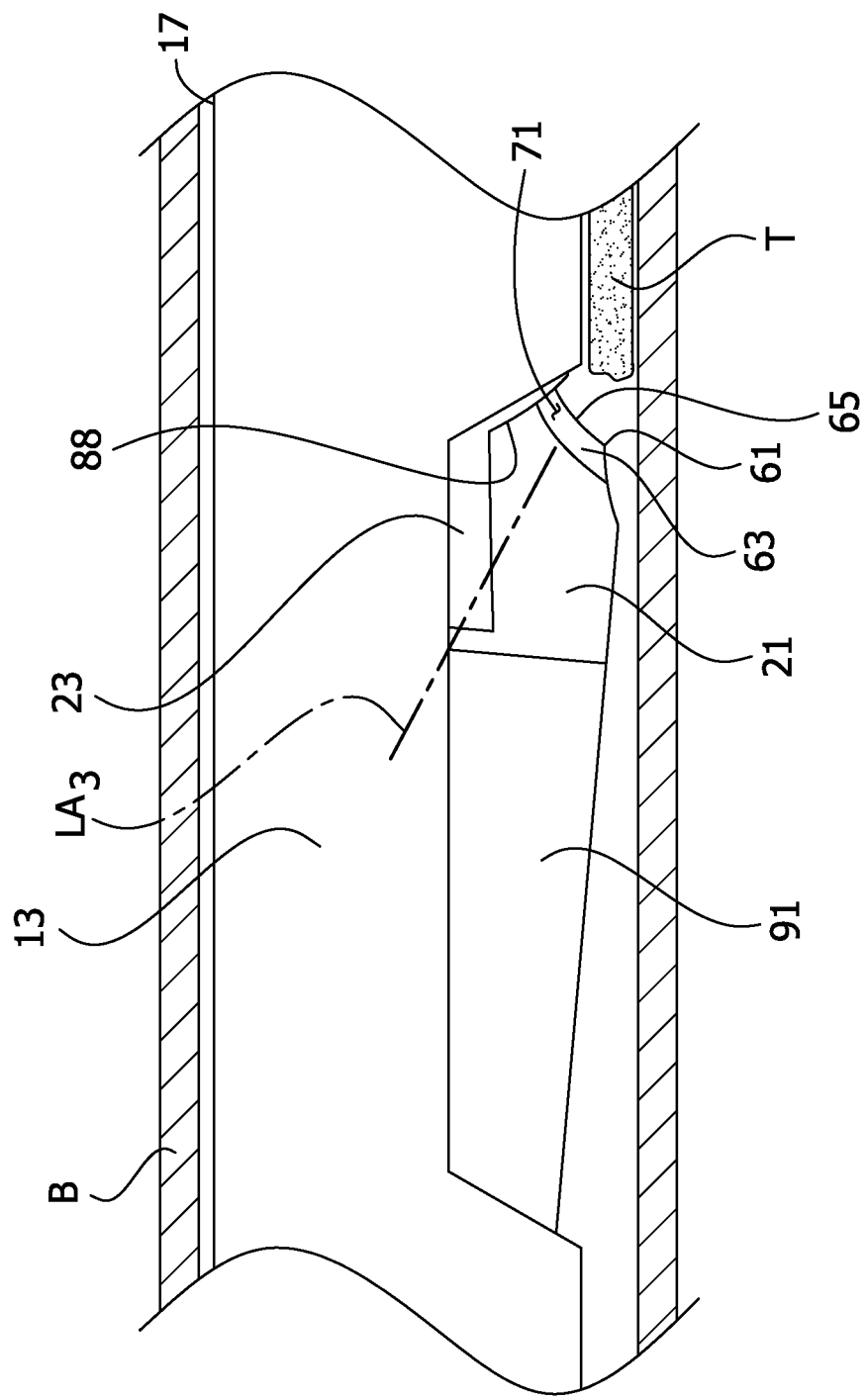
FIGS. 10A-10D are illustrations of the catheter cutting tissue in a body lumen.
Figure 10B:
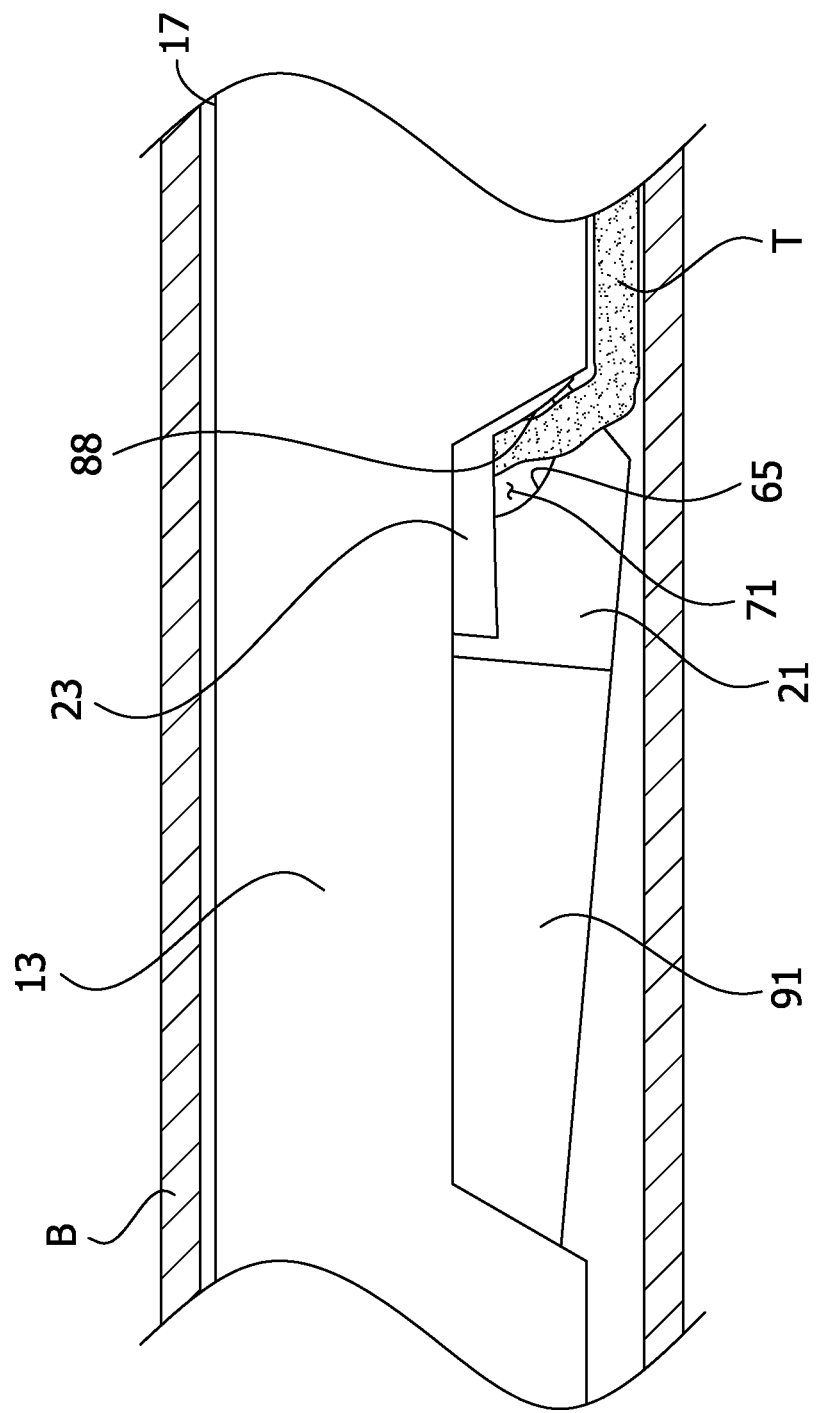
Figure 10C:
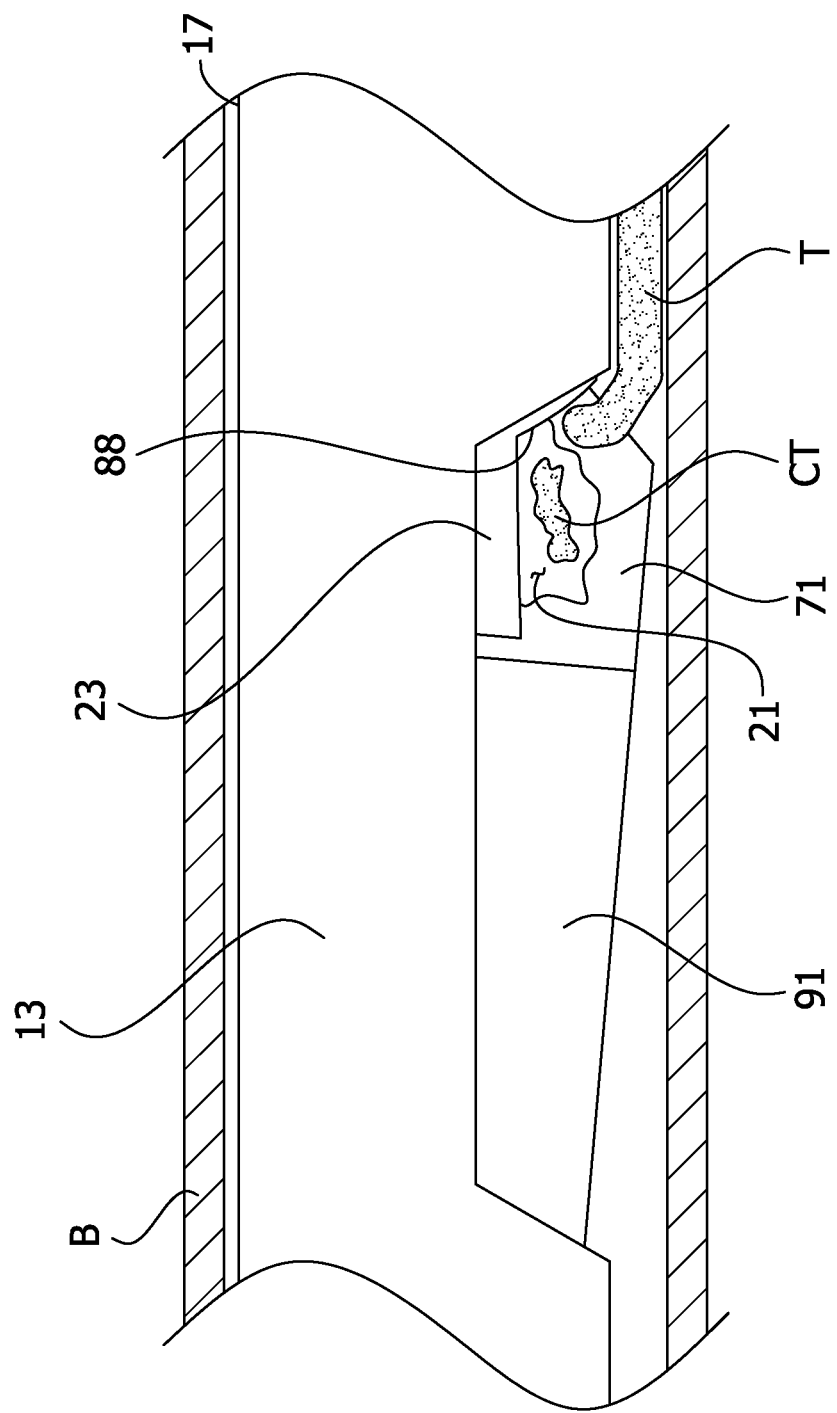
Figure 10D:
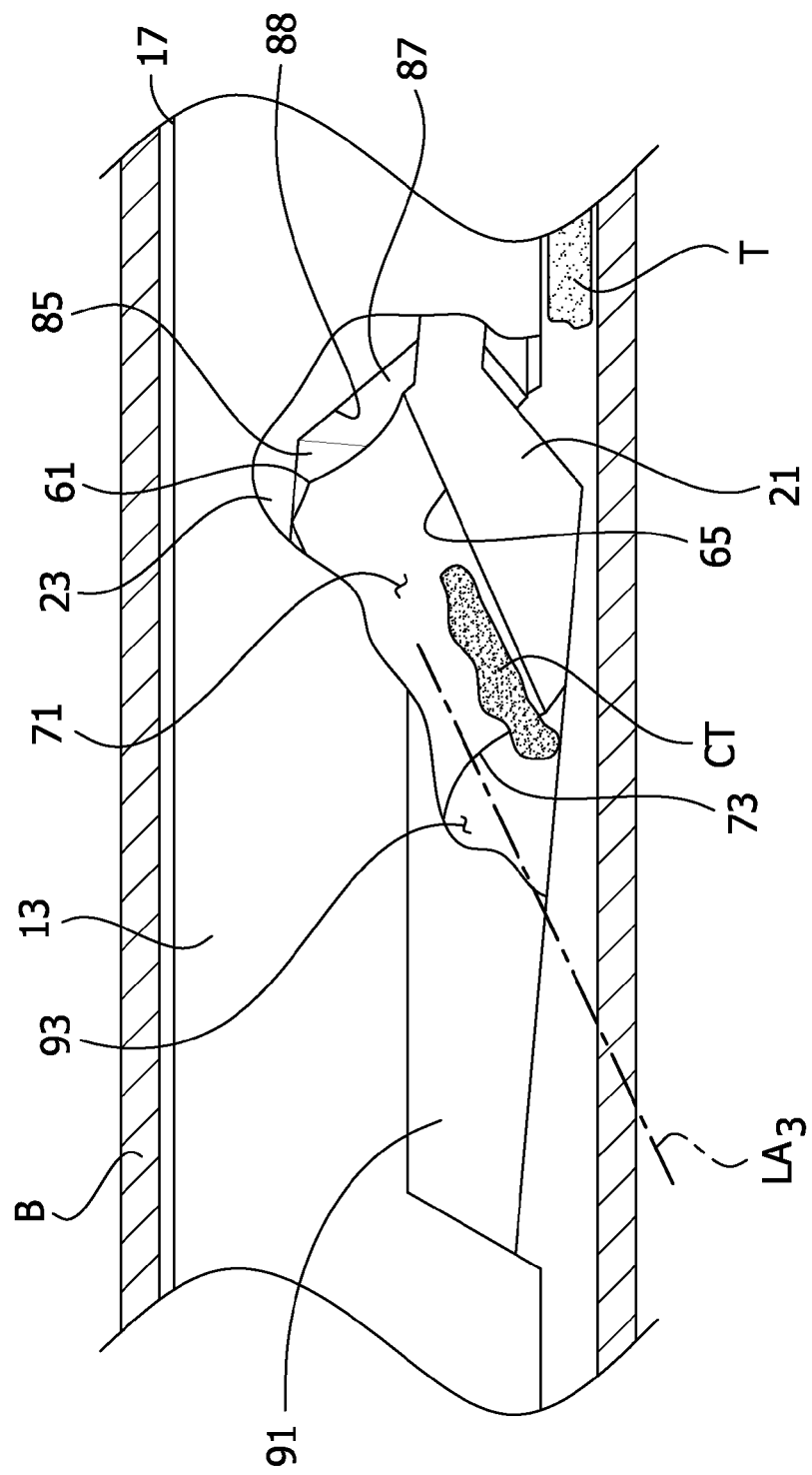

During operation, the distal end 17 of the catheter tube 13 is moved past tissue T in the body lumen B so that the cutter 21 is moved into a position for engaging the tissue (FIG. 10A). As shown in the illustrated embodiment, the tissue T is disposed at a bottom of the body lumen B. As shown in FIG. 4, The longitudinal axis LA₃ of the cutter cavity 71 has a negative slope (i.e., axis increases from right to left) so that the eccentric opening 61 faces the bottom of the body lumen B and the outlet 73 faces a top of the body lumen (as oriented in the drawings). As the catheter tube 13 is being moved, the cutter 21 rotates. When the cutter 21 is moved over the tissue T, the rotation of the cutter causes the cutting edge portion 65 to engage the tissue and pull the tissue away from the bottom wall of the body lumen B (FIG. 10B). This action of the cutter 21 grabs and scoops a section of the tissue T. As the cutter 21 continues to rotate, the tissue T is pulled into engagement with the shearing edge 88 of the bearing 23. Continued rotation of the cutter 21 also reduces the clearance 89 (FIG. 4) between the cutting edge portion 65 and the shearing edge 88 of the bearing 23. As the cutting edge portion 65 of the cutter 21 moves past the shearing edge 88 of the bearing 23, the components cooperate to cut a piece of the tissue CT from the tissue T (FIG. 10C). In particular, the small, substantially zero clearance 89 between the cutting edge portion 65 and the shearing edge 88 when the cutter 21 is in the position shown in FIG. 10C causes the cutting edge portion and the shearing edge to perform a scissor like cutting action to shear off the piece of tissue. The cut tissue CT is then captured in the cavity 71 of the cutter 21 (FIG. 10D). By this time, the cutter 21 has rotated 180 degrees so that the longitudinal axis LA₃ of the cavity 71 has a positive slope (i.e., axis increases from left to right). Therefore, the eccentric opening 61 faces the top of the body lumen B and the outlet 73 faces a bottom of the body lumen (as oriented in the drawings). As a result, the cut tissue CT is funneled down into the interior space 93 of the second bearing 91. The auger 27 in the second bearing 91 will then transport the cut tissue CT to the proximal end 15 of the catheter tube 13 for removal. It is understood that the tissue T could also be cut when the cutting edge portion 65 of the cutter 21 first engages the tissue. In this instance, the cut tissue would still be scooped up into the cavity 71 of the cutter 21 and funneled into the interior space 93 of the second bearing 91 for transport by the auger 27 to the proximal end 15 of the catheter tube 13.

As shown in the illustrated embodiment, the tissue T is located on a bottom of the body lumen B. It will be understood that if the tissue T is located on a top or side of the body lumen B the catheter 11 will function the same as shown except the orientation of the longitudinal axis LA₃ of the cutter cavity 71 may change depending on the position of the catheter 11. However, in each case, the cavity 71 will funnel the cut tissue into the interior space 93 of the second bearing 91 and the auger 27 will transport the cut tissue to the proximal end 15 of the catheter tube 13.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:
1. A catheter comprising:
an elongate catheter body configured for insertion into a body lumen of a subject, the elongate catheter body having opposite distal and proximal ends, a longitudinal axis extending between the distal and proximal ends, and an interior passage extending along the longitudinal axis;

a drive shaft extending longitudinally within the interior passage of the elongate catheter body, wherein the drive shaft is rotatable about its longitudinal axis relative to the elongate catheter body; and a cutter having a proximal end portion, a distal end portion, and a longitudinal axis extending between the proximal and distal end portions, the cutter being located generally at the distal end of the elongate catheter body, wherein the drive shaft is coupled to the proximal end portion of the cutter such that rotation of the drive shaft relative to the elongate catheter body imparts rotation of the cutter about a cutter rotational axis extending through the proximal and distal end portions of the cutter, the cutter further including an eccentric opening in the distal end portion of the cutter defining an angled cutting edge for cutting tissue from a wall of the body lumen, a center of the eccentric opening being offset from the longitudinal axis of the cutter, and a cavity extending from the eccentric opening through the cutter from the distal end portion to the proximal end portion to allow tissue cut by the cutter to pass through the cutter into the interior passage of the elongate catheter body for removal from the body lumen, wherein the cavity extends transversely through the cutter relative to the longitudinal axis of the cutter, wherein the cutter rotational axis is angularly offset relative to the longitudinal axis of the elongate catheter body such that the cutter rotational axis intersects the longitudinal axis of the elongate catheter body at an included angle, wherein the distal end portion of the cutter is disposed within the elongate catheter body.

2. The catheter set forth in claim 1 wherein the center of the eccentric opening is disposed on a longitudinal axis of the cavity, the longitudinal axis of the cavity being skewed with the longitudinal axis of the cutter.

3. The catheter set forth in claim 2 wherein the longitudinal axis of the cavity extends at a 45 degree angle relative to the longitudinal axis of the cutter.

4. The catheter set forth in claim 2 wherein the longitudinal axis of the cavity changes in slope relative to the longitudinal axis of the elongate catheter body as the cutter rotates.

5. The catheter set forth in claim 1 wherein the distal end portion of the cutter has an angled surface, the eccentric opening being formed in the angled surface.

6. The catheter set forth in claim 1 wherein the eccentric opening further defines a leading edge of the cutter, the cutting edge protruding further in a radial direction from the longitudinal axis of the cutter than the leading edge.

7. The catheter set forth in claim 1 further comprising a shearing surface generally opposing at least a portion of the distal end portion of the cutter, the rotation of the cutter causing the cutting edge to move past the shearing surface to shear the tissue in the body lumen.

8. The catheter set forth in claim 7 wherein the shearing surface is fixed relative to the elongate catheter body and the catheter further comprises a bearing received in the distal end of the catheter, the cutter being connected to the bearing allowing for rotation of the cutter relative to the bearing.

9. The catheter set forth in claim 8 wherein the shearing surface is formed in the bearing.

10. The catheter set forth in claim 8 further comprising a second bearing received at least partially in the elongate catheter body and attached to the proximal end portion of the cutter, the second bearing being hollow to allow tissue cut by the cutter to pass from the cutter into an interior space of the second bearing.

11. The catheter set forth in claim 10 wherein the driveshaft extends through the second bearing and the interior passage of the elongate catheter body, the driveshaft having a helical auger for transporting cut tissue toward the proximal end of the elongate catheter body.

12. The catheter set forth in claim 1 wherein the distal end portion of the cutter is generally conical in shape.

* * * * *